(12) United States Patent
Castro

(10) Patent No.: US 8,597,284 B2
(45) Date of Patent: Dec. 3, 2013

(54) COSMETIC REJUVENATION BY PHOTODYNAMIC THERAPY

(75) Inventor: Danilo Castro, Montevideo (UY)

(73) Assignee: Biolitec Pharma Marketing, Ltd., Ft. Labuan (MY)

(*) Notice: Subject to any disclaimer, the term of this patent is extended or adjusted under 35 U.S.C. 154(b) by 314 days.

(21) Appl. No.: 12/792,211

(22) Filed: Jun. 2, 2010

(65) Prior Publication Data
US 2010/0312167 A1    Dec. 9, 2010

Related U.S. Application Data

(60) Provisional application No. 61/183,819, filed on Jun. 3, 2009.

(51) Int. Cl.
*A61B 18/18*  (2006.01)

(52) U.S. Cl.
USPC ............................................................. 606/9

(58) Field of Classification Search
USPC .............................. 606/2, 9–10, 13; 424/401
See application file for complete search history.

(56) References Cited

U.S. PATENT DOCUMENTS

| | | | |
|---|---|---|---|
| 2007/0027411 A1* | 2/2007 | Ella et al. | 601/7 |
| 2007/0166369 A1* | 7/2007 | Neuberger et al. | 424/450 |
| 2009/0112192 A1* | 4/2009 | Barolet et al. | 606/9 |
| 2009/0287195 A1* | 11/2009 | Altshuler et al. | 606/9 |

FOREIGN PATENT DOCUMENTS

RU    2190436 C1 * 10/2002

* cited by examiner

*Primary Examiner* — James Greece
(74) *Attorney, Agent, or Firm* — Bolesh J. Skutnik; BJ Associates

(57) ABSTRACT

A PhotoDynamic Therapy (PDT) method is presented for cosmetic rejuvenation, which is exemplified by a two phase approach for treating facial and neck skin aging while minimizing damage to the underlying region of skin being treated. To obtain best results a combination of treatments are used. This includes applying photosensitizer and light energy for stimulating the collagen within the skin, thereby restoring the elasticity of skin. The treatment procedures take about six weeks consisting of impair (damage) and repair (recovery) sessions involving skin preparation by peeling, skin detoxification, application and distribution of photosensitizer to the skin, irradiation of pre-sensitized skin followed by removal of mask. Results of long lasting improvement, especially in comparison with most cosmetic treatments, are obtained upon completion of the series, with marked changes being observed after individual sessions, which provide added incentive to complete a treatment program. These results eliminate the need for repetitive treatments after the six week series, unlike most current approaches which require repeat sessions semi-annually or annually.

12 Claims, 5 Drawing Sheets

Phase 1 — DAMAGE TREATMENT PROCEDURE

Phase 2 — RECOVERY TREATMENT PROCEDURE

Step 1a: Facial Skin Cleaning

STEP 1b: Skin polishing - brushing and scrubbing

STEP 1c: Micro dermabrasion (Diamond Peel)

STEP 1d: Glycolic Peel

STEP 2: Detoxification

STEP 3 a: Application of photosensitizer

STEP 3 b: Galvanic penetration

STEP 4a: Resting

STEP 4b: Irradiation

STEP 5a: Decongestive Mask

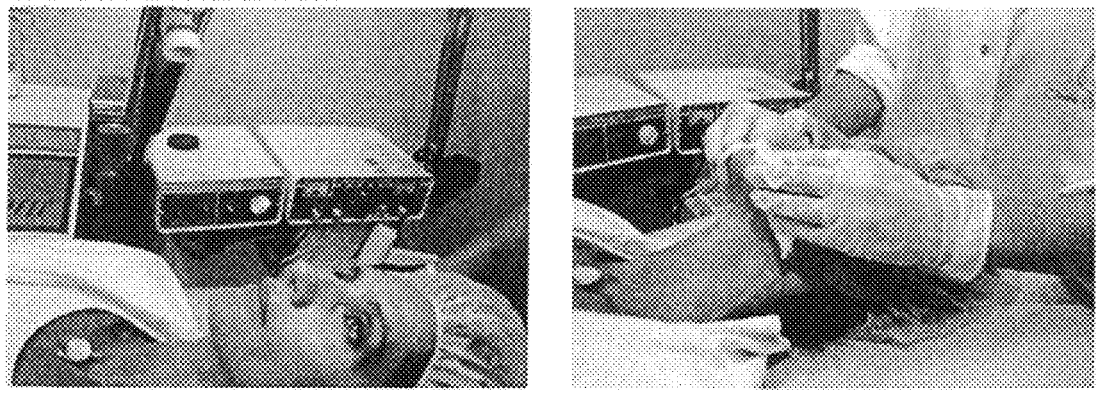
Figure 3 cont'd
STEP 5b: Removal of Mask
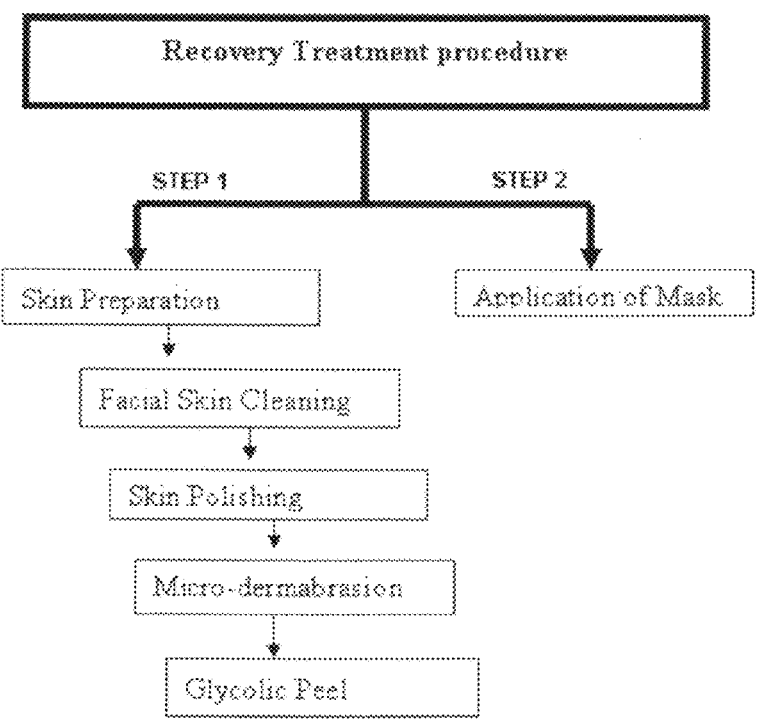

COSMETIC REJUVENATION BY PHOTODYNAMIC THERAPY

DOMESTIC PRIORITY UNDER 35 USC 119(e)

This application claims the benefit and priority of U.S. Provisional Application Ser. No. 61/183,819 filed Jun. 3, 2009, entitled "Cosmetic Rejuvenation by Photodynamic Therapy" by Danilo Castro, which is incorporated by reference herein.

BACKGROUND OF THE INVENTION

1. Field of the invention

Present invention relates to PhotoDynamic Therapy (PDT) and cosmetic treatments in general and, in particular, it relates to use of PDT treatment in cosmetic applications to improve skin conditions for aesthetic purpose.

2. Invention Disclosure Statement

Photodynamic therapy (PDT) is a relatively new treatment modality used in cancer treatment and certain other diseases. PDT's dermatological use has great promise because appropriate photosensitizers or photosensitizer precursors can selectively accumulate in abnormal cells. Exposure to an appropriate wavelength activates the photosensitizer. The activated photosensitizer produces cytotoxic singlet oxygen, in cells that have absorbed the photosensitizer. A variety of cutaneous malignancies and cosmetic problems related to the skin can be treated successfully with PDT.

Skin is the largest organ of the body, accounting for 12% to 16% body weight. Skin is made up of two main layers that cover a third fatty layer. The outer layer is the epidermis, and second layer beneath epidermis is the dermis. Under these two skin layers is a fatty layer of subcutaneous tissue. With age the amount of subcutaneous (under-the-skin) fat is reduced resulting in a looser look to the skin. Skin changes, such as wrinkles and sagging skin, are among the most visible signs of aging. Whitening or graying of the hair is another obvious sign of aging.

The anatomy of a wrinkle begins in the dermis (second major skin layer) where collagen and elastin provide attachment support for the underlying muscles. When collagen, which provides strength, and elastin which provides the resilience for skin, weaken, the surface layer of the skin begins to fall forming a wrinkle. Therefore, healthy collagen and elastin is necessary to provide support, elasticity and firmness to the skin so as to appear smooth and even toned.

A primary cause of wrinkling is sun damage. Fair-skinned people who have prolonged sun exposures usually have skin that is much more wrinkled and weather-beaten than people with dark skin. Aging can be of two types, namely intrinsic aging (genetic factors) and extrinsic aging (external environmental factors).

Dermatologists often use Glogau's classification when describing these aging changes.

Glogau Classification for Skin Aging

1. Glogau soft: minimal wrinkles.
2. Glogau moderated: presence of some wrinkles with motion, such as smile lines.
3. Glogau advanced: persistent wrinkles at rest, skin color changes, ecchimosis and solar keratoses.
4. Glogau severe: many persistent wrinkles, no normal skin.

Fine lines and wrinkles arise because of an irregular thickening of the dermis and a decrease in the amount of water that the epidermis can hold. Sun damage and exposure to environmental toxins, i.e. tobacco smoke, and loss of moisture can cause these skin changes.

Deeper lines or furrows are classified as dynamic or static. Dynamic lines appear while muscles are in movement i.e. the activity of facial muscles. Static lines are unchanged with muscle movement. Eventually dynamic lines become static.

Cosmetic products and procedures are booming industries in our age- and beauty-obsessed culture. Billions of dollars are spent each year on skin care (anti-wrinkle/anti-aging) products that promise to erase wrinkles, lighten age spots or fix another skin malady. Cosmetic surgeries are used to erase wrinkles and to make skin deformities appear younger with toned clear skin.

At present, available treatment for wrinkle reduction and skin rejuvenation includes injectable fillers and botulinum toxin. Both are non-ablative/non-surgical procedures suitable for people with busy lifestyles because of their short recovery time. Fillers are short lived and ineffective. Fillers also cause allergic reaction in many patients.

Different skin peeling (ablative) methods used include chemical, mechanical and photothermal. A chemical peel uses trichloroacetic acid (TCA), other Alpha Hydroxy acids (AHA) and phenol. A mechanical peel, also called transcutaneous blepharoplasty, shaves off the outer layer of skin. In most of these peeling procedures depth of peeling cannot be controlled. Thus the inner skin layer is damaged and exposed to the environment. There is also the possibility of scarring and skin pigmentation.

Photo-thermal peel is an ablative laser skin resurfacing method. A pulsed $CO_2$ laser is used for removing periocular and other types of wrinkles. Pulsed $CO_2$ lasers, used for skin resurfacing, are difficult to apply and can cause valleys and ridges because of inconsistent treatment over a large area with small spot size. Heat diffusion is also difficult to control with pulsed $CO_2$ lasers. Er:YAG lasers have also been used for performing laser skin resurfacing. Er:YAG lasers have a very small penetration depth and thus are not very effective for treating deep wrinkles. Er:YAG skin resurfacing is less painful, less inflammatory and heals quicker, when compared to $CO_2$ lasers. However, Er:YAG is unable to stimulate new collagen growth as effectively as the $CO_2$ laser. Therefore, fine wrinkles are usually not eradicated effectively.

In U.S. Pat. No. 7,198,634, Harth et al. disclose a phototherapeutic method for treating inflammatory skin conditions with combined radiation of infrared radiation and ultraviolet/blue light. The light therapy is used to reduce the inflammation in the skin and increase the blood circulation and faster healing. Here the treatment section for aging generally requires about 5-15 sittings followed by periodic maintenance treatment.

In U.S. Pat. No. 7,066,941, Perricone discloses an apparatus for treating aging or damaged skin by irradiation of affected skin with effective amount of blue and or ultraviolet lights having wavelengths of about 400-500 nm. '941' also discloses application of compositions containing compounds like α-hydroxy acids on skin which reputedly enhance light penetration.

Non-ablative light skin rejuvenation is also immensely popular because of the short healing time. In this method the skin epidermis is, generally, not removed as in the case of ablative laser treatment. One example of non-ablative source is an infrared light source. Non-ablative treatments always require multiple sessions and may take several weeks for optimal results.

Other available treatments include radiofrequency, dermabrasion, micro-dermabrasion and topical treatments to restore skin. The topical treatments give the skin a smoother and refreshed appearance.

PhotoDynamic Therapy (PDT) is a recent advancement in facial rejuvenation using blue light, red light or intense pulse light. During PDT, a photosensitizer is applied to the skin; the skin is then exposed to a light source after a determined period of time during which the photosensitizer is absorbed by the cells. Reported side effects include transient burning, stinging, swelling and redness. Side effects are variable depending on the treatment area, length of photosensitizer exposure and the light source used. Post treatment exposure to light can often create further problems and harm skin.

Unfortunately, all known skin rejuvenation suffers from lack of efficacy and/or from risk to the patient. Hence need remains for a new treatment method, which can be used for skin resurfacing in a painless environment with less potential for scarring and with fast recovery to give a younger and smooth looking skin.

OBJECTIVES AND BRIEF SUMMARY OF THE INVENTION

It is an objective of the present invention to provide a modified PDT treatment in combination with other skin treatment procedures for cosmetic applications.

It is another objective to use a PDT based treatment, for skin rejuvenation to improve aging facial and neck skin for aesthetic purpose.

It is also an objective to use a modified PDT method to stimulate collagen production to fill the deep wrinkles on the skin and to give smoother looking skin.

It is likewise an objective of the present invention to eliminate superficial flabbiness and deep flabbiness.

It is yet a further objective of the present invention to reduce the number of treatment sessions involved.

Briefly stated, the present invention provides a modified PhotoDynamic Therapy (PDT) method for cosmetic rejuvenation, exemplified by a two phase approach for treating facial and neck skin aging while minimizing damage to the underlying region of skin being treated. To obtain best results a combination of treatments are used. This includes applying photosensitizer and light energy for stimulating the collagen within the skin, thereby restoring the elasticity of skin. The treatment procedures take about six weeks consisting of paired impair (damage) and repair (recovery) sessions involving skin preparation by peeling, skin detoxification, application and distribution of photosensitizer to the skin, irradiation of presensitized skin followed by removal of mask. Results of long lasting improvement, especially compared to most cosmetic treatments, are obtained upon completion of the series, with marked changes being observed after individual sessions, which provide added incentive to complete the treatment program. These results eliminate the need for repetitive treatments after the six week series, unlike most prior art solutions which require repeated sessions semi-annually or annually.

The above and other objects, features and advantages of the present invention will become apparent from the following description read in conjunction with the accompanying drawings, (in which like reference numbers in different drawings designate the same elements.)

BRIEF DESCRIPTION OF FIGURES

FIG. 4 illustrates a diagrammatic representation of different steps involved in Recovery Phase Treatment.

DETAILED DESCRIPTION OF PREFERRED EMBODIMENTS

The present invention describes a novel method, applying a modified PhotoDynamic Therapy (PDT) in combination with a number of other procedures, for cosmetic treatment of aged and/or damaged skin. This method enhances appearance of skin by improving texture and tone.

Present invention can also be used to for treating acne, remove/minimize the acne scar marks, improves skin texture, reduced pore size, even removes fine wrinkles, reduces hyperpigmentation and other associated skin problems.

The method rejuvenates skin with less destruction, scarring and pain, compared to deeper peels and other current laser procedures. Subsequently, the recovery time is reduced during the post treatment period.

PDT is used in combination with other treatments to obtain best aesthetic results. The method is especially designed to improve the effects of aged facial and neck skin including superficial and deep flabbiness, wrinkles, lines and furrows.

Figure 1:
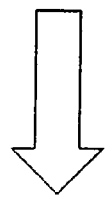
FIG. 1 illustrates a diagrammatic representation of treatment phases.

The method applies one of two weekly treatments for a minimum of six weeks. The treatment phase includes damage (impair) and recovery (repair) procedures (FIG. 1). Each treatment phase consists of several steps. A primary benefit of the six week treatment series is long lasting improvement obtained upon completion of the series. These results eliminate the need for semi-annual/annual repetitive/maintenance treatments after the six week series, which are typical for most cosmetic treatments. Furthermore, marked changes are observed after every individual session. This has a beneficial effect on patient attitude and may increase patient adherence to the six week treatment series.

Figure 2:
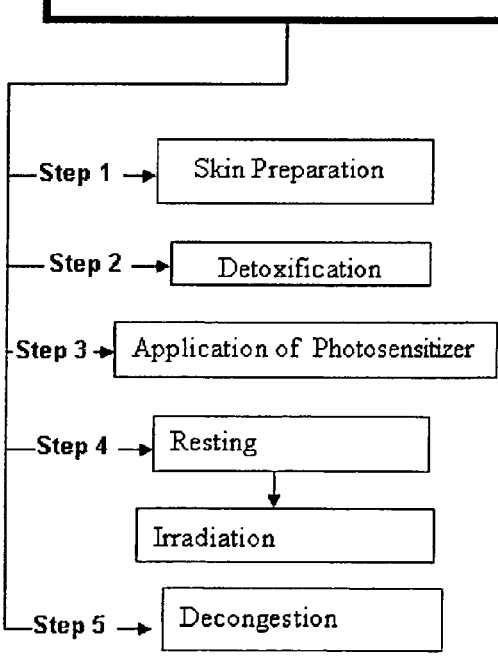
FIG. 2 illustrates the different steps involved in Damage Procedure Treatment.
Figure 3:
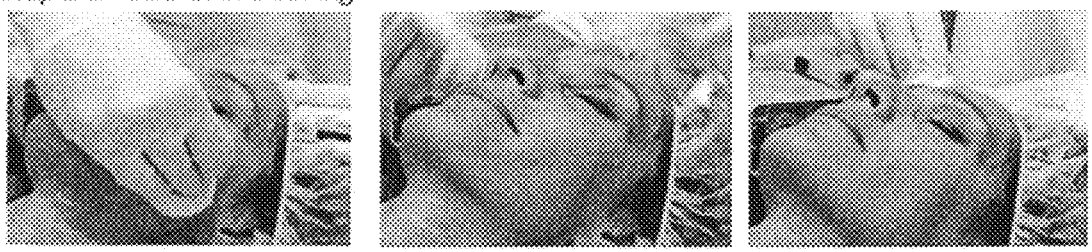
FIG. 3 presents photographs of different steps involved in Damage Treatment Procedure.
Figure 3:
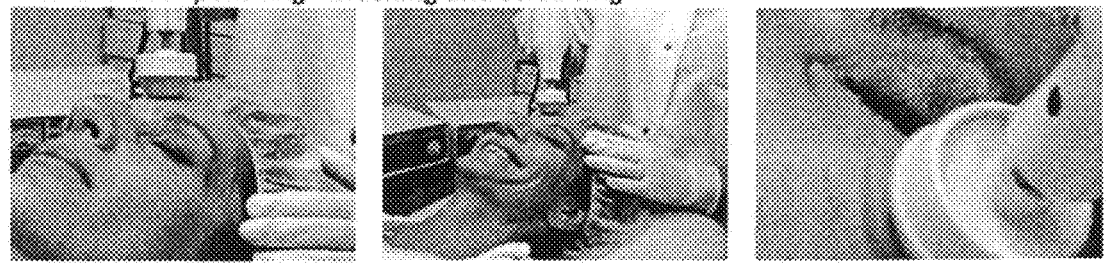
Figure 3:
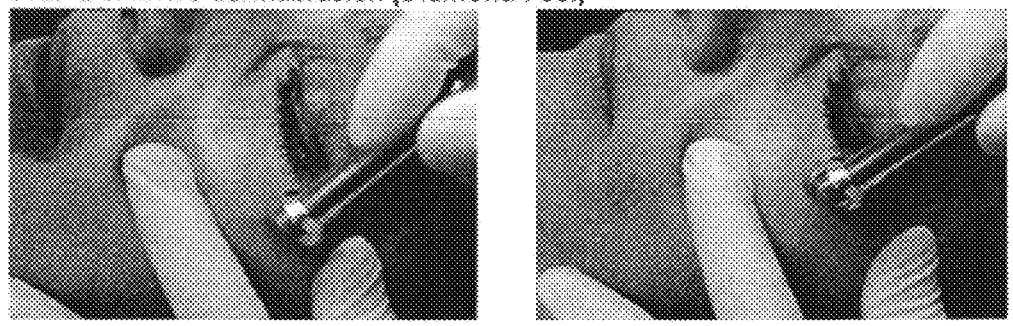
Figure 3:
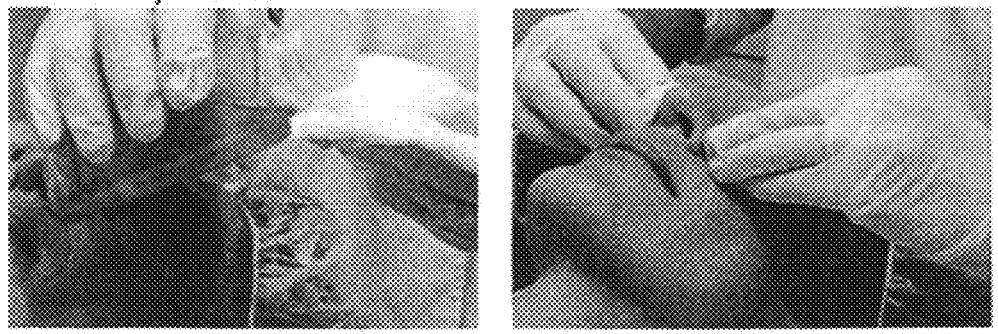
Figure 3:
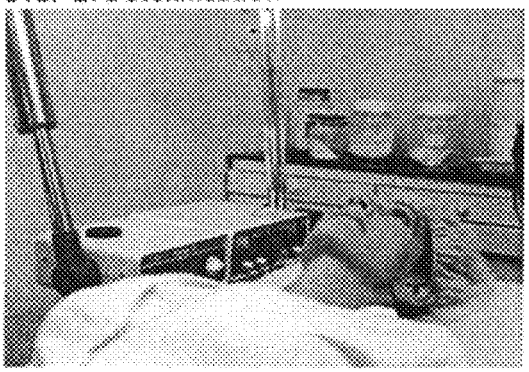
Figure 3:
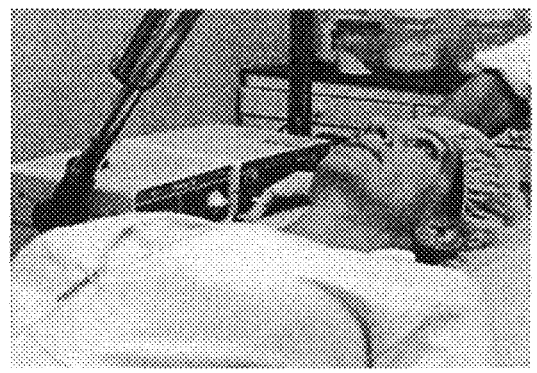
Figure 3:
Figure 3:
Figure 3:
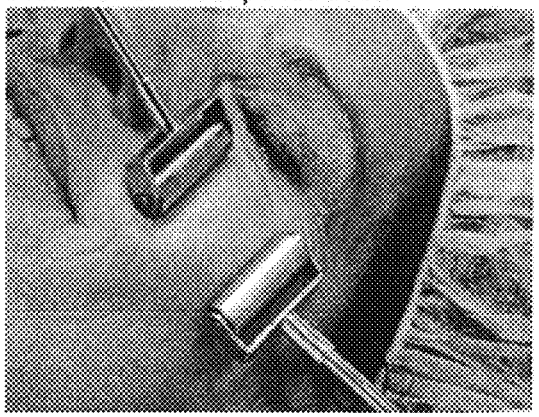
Figure 3:
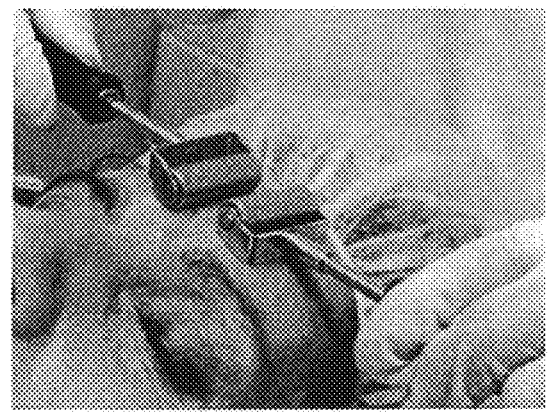
Figure 3:
Figure 3:
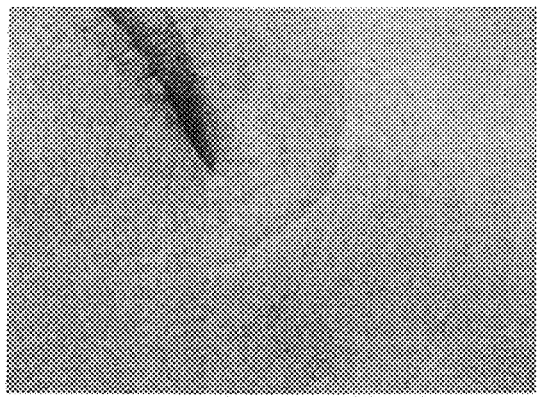
Figure 3:
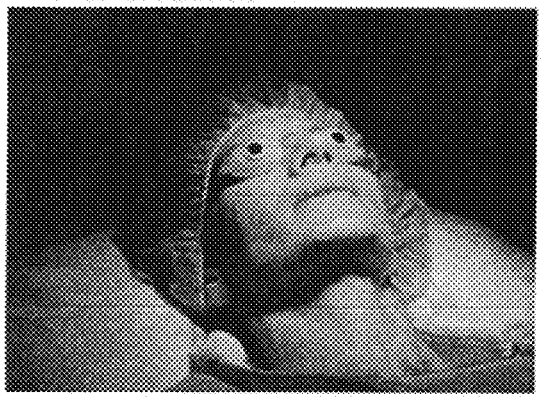
Figure 3:
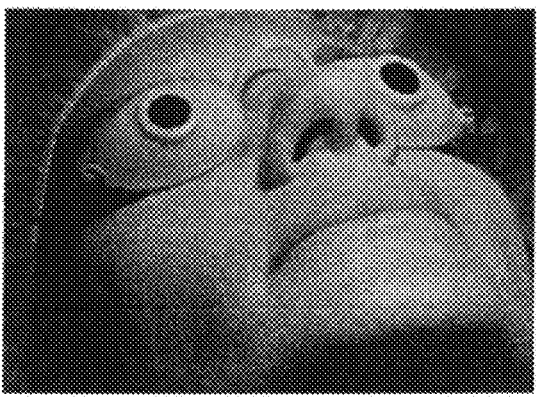
Figure 3:
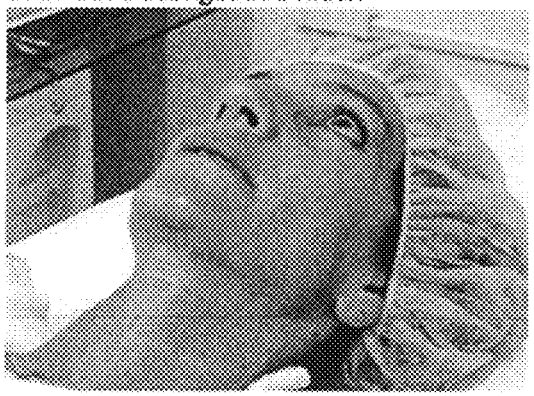
Figure 3:
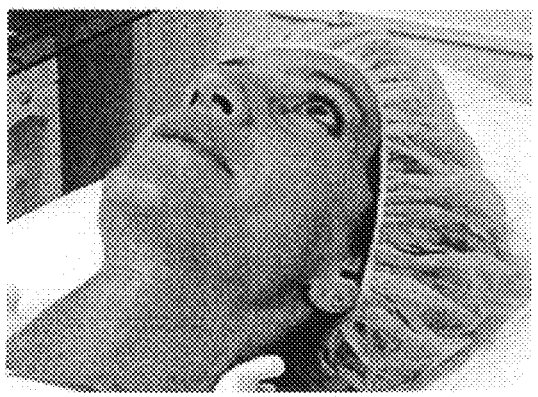

FIG. 2 diagrammatically illustrates different steps in the damaged treatment procedure phase of the treatment and FIG. 3 shows the photographs of steps involved during the procedure.

In a preferred embodiment, the steps of the Damage (Impair) Treatment procedure are: (FIGS. 2 and 3)
Step 1: Skin Preparation and Peel
a) Facial skin cleaning
b) Skin polishing-scrubbing and brushing
c) Micro-dermabrasion—using diamond point or diamond peel
d) Glycolic peel using Glycolic Acid 15% application
Step 2: Detoxification
a) Fifteen minute ozone vapor facial sauna
Step 3: Application and Distribution of Photosensitizer
a) Photosensitizer application
b) Ten minute galvanic penetration electricity application
Step 4: Rest and Photosensitizer Activation
a) 15 minute rest
b) 15 minute photosensitizer activation with light energy
Step 5: Decongestion
a) 10 minute decongestive mask application
b) Mask removal In general not all sub-steps are necessary for all treatments, depending on level of damage needed to be removed from the complete treatment. Additionally, the exact period of time for each step and sub-step will be determined according to the therapeutic effect to be achieved, the patient's skin type and condition, age, photo damage and others.

Steps 1 and 2 (see FIG. 3) above are designed to prepare the skin to enhance photosensitizer absorption Skin preparation and Detoxification steps (FIG. 3, step 2) also improve the skin condition to some extent as this removes dead epithelial cells from the skin surface, and also removes tans thus improving skin complexion and since superficial upper layer is being removed the skin now appears softer and smoother comparatively. The skin condition is altered by opening of skin pores which facilitates drug permeation into lower layer of skin. Step 1a-1d and step 2 opens skin pores to improve penetration of photosensitizer into skin. This is followed by step 3 (FIG. 2) topical application of photosensitizer and application of galvanic electricity (see FIG. 3, step 3a and 3b) to further improve the drug permeation into the skin.

The initial skin preparation method, followed by topical application of the photosensitizer, presents distinct advantages over previous techniques, which were primarily injections using needles. Advantage of topical application of photosensitizer (FIG. 3 Step 3a) avoids pain and anxiety associated with multiple injections using needle systems. Topical application enhances photosensitizer treatment coverage as it is uniform. Applying the photosensitizer over an area of skin covers the skin completely. On the other hand, local injections are likely to cause untreated skin areas between injection sites or overtreatment where overlaps occur. Moreover, photosensitizer introduction requires less skill when applied topically because of the decreased likelihood of insufficient treatment coverage. Finally, it is easier and safer to test patients' sensitivity to photosensitizers with a topical product. The photosensitizer can be applied to a small patch of skin and observed, as opposed to an injection.

In one embodiment, the photosensitizer is formulated into liposome vesicles which would further enhance the drug penetration through the skin membrane.

FIG. 3, photographic pictures show patient resting (step 4a) (Drug-Light-Interval (DLI)) for a short period of 15 minutes. After DLI of 15 minutes skin is irradiated with a wavelength matching the absorption spectrum of used photosensitizer for 15 minutes.

This is followed by Step 5a and 5b (see FIG. 3) wherein a decongestion mask is applied to treated skin regions for 10 minutes. This mask has soothing and repairing effect. This improves microcirculation, subsides erthyma, redness if any associated with damage treatment. After a short interval decongestive mask is removed.

The PDT treatment procedure of the present invention gently stimulates or inhibits cellular activity to reduce the signs of aging. PDT action improves collagen cross-linking and collagen formation thus filling up the furrow and ridges in the skin to reduce deep as well as fine wrinkles and to give a better skin texture with an even skin tone and smoother appearance. It also reduces the effects of free-radical which can cause skin damage.

Damage treatment phase is followed by a skin repairing step referred as the recovery treatment phase (repair phase). The damage treatment phase prepares the skin for the repair treatment phase thus the effect of the procedure is enhanced when compared to other prior art PDT and photo-cosmetic treatments.

The procedures of the recovery (repair) treatment phase (see FIG. 4) include the following steps:
1. Skin Preparation and Peel
 a. Facial skin cleaning
 b. Skin polishing-scrubbing and brushing.
 c. Diamond point or diamond peel micro-dermabrasion
 d. Glycolic Acid 15% application
2. Tensor Mask Application A Tensor mask is applied to skin which has a soothing effect on the treated skin regions. This mask subsides the redness and burning sensation felt immediately after the treatment it also improves blood circulation and hastens healing process of skin.

Having described preferred embodiments of the invention with reference to the accompanying drawings, it is to be understood that the invention is not limited to the precise embodiments, and that those skilled in the art can effect changes and modifications without departing from the scope of the invention as defined in the appended claims.

What is claimed is:

1. A two phase photo-enhanced, cosmetic rejuvenation method for skin rejuvenation wherein fine lines and deep wrinkles are treated, comprising:
 a damage/impair phase for opening skin pores to facilitate absorption of a phosensitizer into the skin in preparation for skin irradiation, comprising the steps of:
  a) skin preparation and peel;
  b) detoxification;
  c) application and distribution of photosensitizer;
  d) rest and photosensitizer activation; and
  e) decongestion;
 wherein said step of skin preparation and peel comprises at least two steps selected from the group consisting of:
  a. facial skin cleansing;
  b. skin polishing;
  c. micro-dermabrasion using diamond point and diamond peel; and
  d. glycolic peel using 15% glycolic acid; and
 a recovery/repair phase for hastening healing of the skin.

2. The rejuvenation method according to claim 1, wherein the step of said skin polishing comprises one of the following:
 a. brushing with a paste;
 b. polishing with a paste;
 c. brushing with a scrub; or
 d. polishing with a scrub.

3. The rejuvenation method according to claim 1, wherein the step of said detoxification comprises an ozone vapor facial sauna.

4. The rejuvenation method according to claim 1, wherein the step of said application and distribution of photosensitizer comprises application of galvanic penetration electricity.

5. The rejuvenation method according to claim 1, wherein the step of said rest and photosensitizer activation comprises:
 a) resting for a predetermined period of time; and
 b) activating said photosensitizer with light energy attuned to absorption of said photosensitizer.

6. The rejuvenation method according to claim 1, wherein the step of said decongestion comprises:
 a. decongestive mask application; and
 b. mask removal.

7. The rejuvenation method according to claim 1, wherein said recovery/repair phase comprises the steps of:
 a. skin preparation and peel; and
 b. tensor mask application.

8. The rejuvenation method according to claim 7, wherein said step of skin preparation and peel comprises at least one of the following:
 a. facial skin cleaning;
 b. skin polishing;
 c. micro-dermabrasion; wherein the said micro-dermabrasion uses diamond point and diamond peel; and
 d. glycolic peel using 15% glycolic acid.

9. The rejuvenation method according to claim 8, wherein said skin polishing comprises one of the following:
   a. brushing with a paste;
   b. polishing with a paste;
   c. brushing with a scrub; or
   d. polishing with a scrub.

10. The rejuvenation method according to claim 1, wherein said rejuvenation method is used for at least one of the following skin treatments:
   treating acne, removing/minimizing acne scar marks;
   improving skin texture;
   reducing pore size;
   removing fine wrinkles;
   reducing hyper-pigmentation; and
   other associated skin aging problems.

11. The rejuvenation method according to claim 1, wherein the photosensitizer is applied to areas to be treated in a topical formulation.

12. The rejuvenation method according to claim 1, wherein facial and neck skin are particularly rejuvenated/treated.

* * * * *